US00PP07787P

United States Patent [19]

Drewlow

[11] Patent Number: Plant 7,787

[45] Date of Patent: Feb. 11, 1992

[54] IMPATIENS PLANT NAMED CHARADE

[75] Inventor: Lyndon W. Drewlow, Ashtabula, Ohio

[73] Assignee: Mikkelsens, Inc., Ashtabula, Ohio

[21] Appl. No.: 606,841

[22] Filed: Oct. 31, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A new and distinct cultivar of Impatiens plant named Charade, characterized by its large salmon flowers; deep reddish-purple ovaries; green leaves with a deep purple cast and red midribs and venation; slightly serrated leaf margins; excellent self-branching; and its intermediate height.

1 Drawing Sheet

The present invention comprises a new and distinctive cultivar of Impatiens plant, botanically known as Impatiens, and referred to by the cultivar name Charade. The new cultivar was developed by me through controlled breeding by crossing Mikkelsen Seedling No. 87-173-4 (seed parent) with Mikkelsen Seedling No. 87-418-2 (pollen parent).

Asexual reproduction by terminal or stem cuttings has shown that the unique features of Charade are stabilized and are produced true to type in successive propagations.

The following combination of characteristics distinguish Charade from both its parent varieties and other cultivated Impatiens of this type known and used in the floriculture industry. Characteristics are described with reference to the comparison cultivars Nebulous, disclosed in U.S. Plant Pat. No. 7,097, and Quasar, disclosed in U.S. Plant Pat. No. 5,780. Color references are to The Royal Horticultural Society Colour Chart (RHS).

1. Charade has salmon flowers (39A), with Nebulous having a salmon orange (35A) flower, and Quasar having a salmon rose flower (41C-40D).
2. Charade has a larger flower (6.0 to 6.5 cm in diameter), while Quasar has a 5.0 to 5.5 cm flower diameter and Nebulous has a 5.5 to 6.0 cm flower diameter.
3. Charade has the deepest reddish purple ovaries, while Nebulous has a slight red cast to the ovaries and Quasar has green ovaries.
4. Charade has green stems with a reddish cast which is intermediate beteween Quasar which has a slight red tint to its green stems, and Nebulous which has reddish purple stems.
5. Charade has leaves that have a deeper purple cast than the leaves of Nebulous, with Quasar having green leaves with cream variegation around the midrib of the leaf and the basal end of the leaf. Charade and Nebulous are non-variegated.
6. Charade has leaf margins that are very slightly serrated while Nebulous has an entire leaf margin and Quasar has a serrated leaf margin.
7. Charade and Nebulous have similar size leaves, with the leaves of Charade being 10–11 cm long by 3.0 to 3.5 cm wide, and the leaves of Nebulous being 10–12 cm long by 3 to 4 cm wide. Quasar has smaller leaves, 6.0 to 6.5 cm long and 3.5 to 3.75 cm wide.
8. Charade and Nebulous have red midribs and venation, while Quasar has green venation and cream variegation in the midrib and green outside of the variegation.
9. Charade and Nebulous are similar in blooming date, but 4 to 7 days earlier than Quasar.
10. Charade is in intermediate height mounded growing plant with excellent self-branching, with Nebulous being a larger, more open growing plant, and Quasar a more compact growing plant.

The accompanying colored photograph illustrates in front perspective view the overall appearance of Charade and showing the colors as true as reasonably possible to obtain in a colored reproduction of this type. The photograph was taken in December 1989 under natural light on an overcast day under double poly greenhouse covering at Ashtabula, Ohio.

The following is a detailed description of Charade, based on plants produced in greenhouses in Ashtabula, Ohio during the summer season of the year. Plants were grown in 15 cm pots and measurements were taken 16 weeks after rooted cuttings were planted. Height measurements were taken from the soil line of the container. The plants were grown as 65°–68° F night temperatures, under 3500 to 4500 foot candles of light, and 240 ppm nitrogen, 240 ppm potassium, and 175 ppm phosphorous nutritional levels with trace elements added. Habit of growth, foilage coloration, leaf variegation, size of leaves and flower size will be greatly influenced by nutritional and environmental conditions. Color references are made to The Royal Horticultural Society Colour Chart (RHS) except where general terms of ordinary dictionary significance are used.

Parentage: A controlled cross between female Mikkelsen Seedling No. 87-173-4 and male Mikkelsen Seedling No. 87-418-2.

Propagation:

A. *Type cutting.*—Stem 15 mm long will develop to 4 to 5 cm long in 18 to 21 days.

B. *Time to initiate roots.*—8–10 days at 23° C. summer; 10–12 days at 20° C. winter.

C. *Rooting habit.*—Heavy, fibrous.

Plant description: Habit of growth, foliage coloration and size of leaf will be greatly influenced by nutritional and environmental conditions. Thus, data that follows was taken from plants grown under the conditions stated above.

A. *Form and habit of growth.*—Mounded; intermediate in height; highly self-branched; continuous flowering; flowering over the top of leaf canopy; vigorous growing, flowering herb.

B. *Foliage description.*—Dark green leaves with deep purplish cast; midrib, petiole and underside of leaf are purple-red in color. No foliar variegation. 1. Size: Mature leaves are 10 to 11 cm long and 3.0 to 3.5 cm wide. 2. Shape: Lanceolate with acuminate apex. 3. Texture: Both upper and lower surfaces are glabrous. 4. Margin: Slightly serrated. 5. Color: Young foliage top side, 147A; under side 185B. Mature foliage top side 147A with 185B cast; under side 185A. 6. Venation: Pinnate; red-purple in color.

Flowering description:

A. *Flowering habits.*—Flowers continuously from leaf whorl in a progressively orderly manner, usually with two flowers per leaf axil. All first flowers in a whorl open before the second flower in the leaf axil of that whorl starts to open. When second flowers of a leaf axil start to open the first flower of a leaf axil of whorl above starts to open. It takes 5 to 7 days for a mature bud to fully open, with the flowers lasting two weeks or longer depending on the environment.

B. *Natural flowering season.*—Indeterminant and continuous. Quantity of flowering increases with increasing levels of light.

C. *Flower buds.*—Ellipsoidal, flowers perfect. Green with red cast spur up to 5 cm long with brighter green tip on mature bud, with the throat behind the ovary and originating from the major sepal.

D. *Flowers borne.*—Individual green pedicels with reddish cast from a whorl of 5 to 6 leaves, flowering progressively around the whorl as buds and leaves develop. Most leaf axils have two flowers.

E. *Quantity of flowers.*—Very floriferous because of highly self-branching nature of plant; long lasting flowers and two flowers per leaf axil result in flowers open at three leaf whorls at a time.

F. *Diameter of flower.*—6.0 to 6.5 cm.

G. *Petals.*—1. Shape: Heart-shaped with keel being largest petal. 2. Color: Top side when opening 39A, fading to 39B to 39C; under side 39B. 3. Number of petals: Five. 4. Size of petals: Standard — 3.5 cm wide by 2.8 cm long; two equal, shallow cut lobes. Wings — 2.6 cm wide by 3.1 cm long; two unequal, intermediate cut lobes. Keel — 3.1 cm wide by 3.6 cm long; two unequal intermediate cut lobes.

H. *Reproductive organs.*—1. Stamens: Five in number. Anther shape is hooded; color reddish-purple; pollen color cream. 2. Pistils: Stigma shape is five segmented column; color reddish purple. Style color white with reddish cast. Ovaries, five in number 4 mm mature size; color green with reddish purple cast.

Disease resistance: No significant disease and insect problems noted to date.

OTHER IMPORTANT CHARACTERISTICS

1. Charade has shown the ability to continuously flower under high temperatures and high sunlight, as well as cool temperatures (40°-50° F.). Thus, growing season can be expanded.
2. Early flowering, self-branching nature allows cultivar to be grown in a 10 cm pot. However, Charade is vigorous enough so that it can be grown in 15 to 25 cm containers.

I claim:

1. A new and distinct cultivar of Impatiens plant named Charade, as illustrated and described.

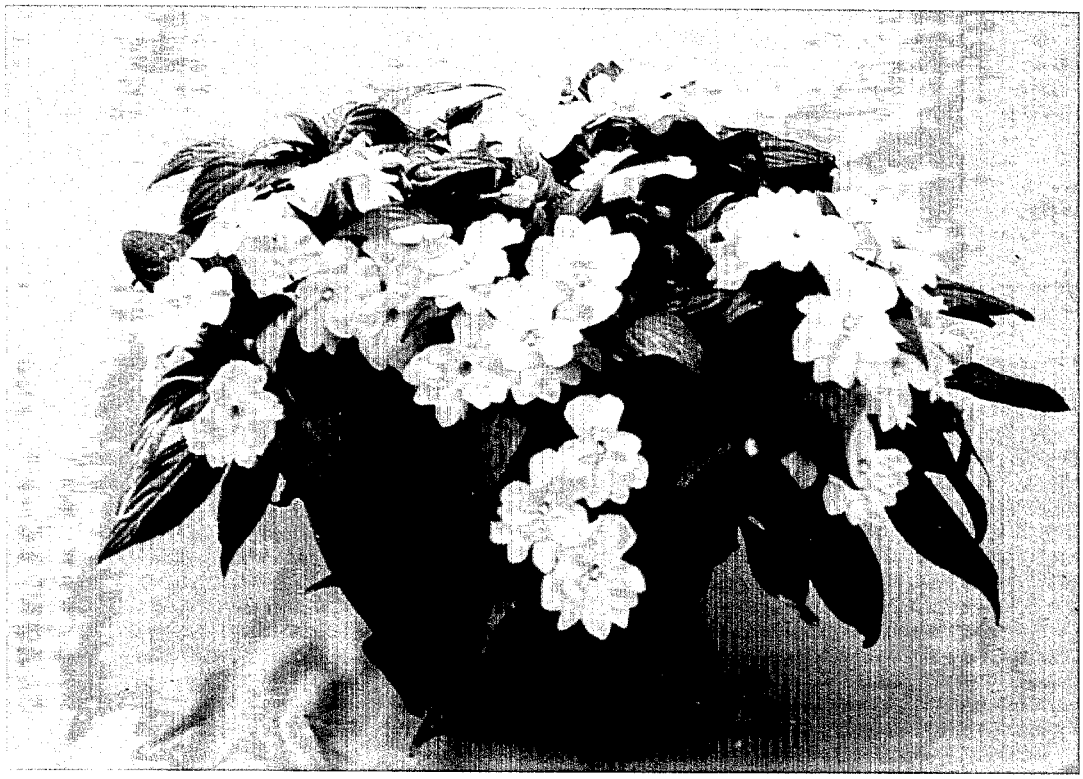

* * * * *